United States Patent [19]

Fedorka-Cray et al.

[11] Patent Number: 5,476,016
[45] Date of Patent: Dec. 19, 1995

[54] APPARATUS FOR ANNOTATING DATA ON AN ASSAY MEDIUM

[75] Inventors: Paula J. Fedorka-Cray; William C. Cray, Jr., both of Ames, Iowa

[73] Assignee: Board of Regents of the University of Nebraska, Lincoln, Nebr.

[21] Appl. No.: 143,919

[22] Filed: Oct. 27, 1993

[51] Int. Cl.⁶ ............................ G01D 15/28; G01N 37/00
[52] U.S. Cl. .............................. 73/863; 422/58; 422/61; 422/119; 436/808; 378/162
[58] Field of Search ........................ 73/863, 866.3; 378/162, 164; 435/7.95; 436/808; 422/58, 61, 119

[56] References Cited

U.S. PATENT DOCUMENTS

| | | | |
|---|---|---|---|
| 456,396 | 7/1891 | Blakemore | 378/165 X |
| 1,229,527 | 6/1917 | Rundle | |
| 1,904,234 | 4/1933 | Hoskin et al. | 378/164 X |
| 2,344,824 | 3/1944 | Landis et al. | 378/164 |
| 3,336,682 | 8/1967 | Genin | 40/614 X |
| 3,591,804 | 7/1971 | Minasian | |
| 3,639,764 | 2/1972 | Olson et al. | |
| 4,045,897 | 9/1977 | Gates | |
| 4,708,931 | 11/1987 | Christian | 422/58 X |
| 4,764,948 | 8/1988 | Hurwitz | 378/162 X |
| 4,918,715 | 4/1990 | Krupnick et al. | 378/164 |
| 4,943,522 | 7/1990 | Eisinger et al. | 422/58 X |
| 4,993,056 | 2/1991 | Lary | 378/164 |
| 5,002,735 | 3/1991 | Alberhosky et al. | 422/58 X |
| 5,020,088 | 5/1991 | Tobin | 378/164 |
| 5,116,576 | 5/1992 | Stanley | 422/58 X |
| 5,238,652 | 8/1993 | Sun et al. | 422/61 |

*Primary Examiner*—Thomas P. Noland
*Attorney, Agent, or Firm*—Merchant, Gould, Smith, Edell, Welter & Schmidt

[57] ABSTRACT

The present invention includes an apparatus, kit and method for annotating information on an assay medium, such as an electrophoresis gel, thin-layer chromatography plate, x-ray film, and the like, prior to recording the data on the assay medium by photography or other like means. The apparatus is composed of a planar base with grooved tracks, or of two or more side rails that are placed on a planar base adjacent the assay medium, with markers for designating information about a sample or its separated components on the assay medium.

27 Claims, 4 Drawing Sheets

APPARATUS FOR ANNOTATING DATA ON AN ASSAY MEDIUM

FIELD OF THE INVENTION

The present invention generally relates to an apparatus, kit and method for annotating data on an assay medium prior to being recorded by photographing, videotaping, digital scanning, photocopying and the like.

BACKGROUND OF THE INVENTION

Chemical, biological, agricultural and related materials are examined using various analytical methods. These methods include techniques for separating or identifying samples and their individual components on various media, such as electrophoresis and thin layer chromatography (TLC), or related charts obtained following chromatography, immunoblots, densitometric scanning, dot blots, and related techniques. With electrophoresis and TLC, a sample is placed at one end of an assay medium such as a polyacrylamide gel or silica gel plate, and an electric field or organic solvent is applied to cause the sample to migrate and separate according to size across the medium. With immunoblots and dot blots, a sample is transferred, with or with prior separation, to an inert media prior to chemical analysis.

In electrophoresis, polyacrylamide, agarose gel or other gel matrices are prepared by pouring a liquid mixture into a chamber, and a comb-shaped form is then inserted to form discrete wells in the upper end of the gel. Test samples are then placed into the wells, and a uniform electric potential is applied to the gel. A mixture of molecular weights standards is typically placed into one well as a control. The negatively charged molecules migrate from the wells in lanes toward the anode at the lower end of the gel slab. Individual components of the samples and standards become separated as bands as smaller molecules move rapidly through the gel and larger molecules move slowly or remain at the upper end of the gel slab. Upon completion of the electrophoretic separation, the gel slab is removed from the chamber and stained with an appropriate dye or other visualizing agent, and illuminated to reveal the separated molecules on the gel. Optionally, the molecules on the gel may be transferred to a second assay medium such as a nitrocellulose membrane, for further analysis by Southern blot, Northern blot, Western blot, isoelectric gels, autoradiographic films, elispots, slot/dot blots, densitometric scans, or other like assay.

The assay medium is then photographed to make a permanent record of the results of the separation. The photograph is subsequently marked on its face to show the lanes associated with each sample, and identify the locations of the separated bands of molecules on the assay medium, usually according to molecular weight as compared to the molecular weights standards, used as the control.

At present, a photograph is marked using permanent ink, radioactive ink, non-radioactive phosphorescent or fluorescent markers, dry-transfer symbols, tape labels, or a frame with attached labels. One commercially-available product from Diversified Biotech, IDENTI-KIT™, includes adhesive labels, numbers and letters for radioactive work which are either permanently affixed by light development following development of the X-ray film, or affixed after development of the X-ray film at which time the markers may be reused.

Marking individual photographs with lane information and sample locations is an arduous task, particularly where a scientific report or publication contains numerous photographs of electrophoresis gels. In addition, a written record must be kept of the locations of the sample lanes, and positions of the molecular standards, or other pertinent information, so that this information can later be transferred to the photograph. Another disadvantage is that if more copies of a marked photograph are needed, the marked copy must be either rephotographed and printed wherein there is often a reduction in clarity of the photograph, or another copy of the original photograph must be labeled with a second set of markers. Also, markers that are permanently affixed to the photograph cannot be reused in multiple applications, and releasably-adherent markers have a limited lifetime for reuse. Still another drawback of present marking systems is that a photograph with an error in the marking must be discarded and the marking process repeated to prepare a newly marked photograph. Also, if it is desirable to eliminate a sample lane from the assay medium or rearrange the lanes in relation to each other, the photograph must be cut up, carefully reassembled, and then rephotographed.

Therefore, an object of the invention is to provide an apparatus and method, to facilitate annotating an assay media containing samples. Another object is to provide an apparatus for use in multiple applications, and which shorten the annotating process. Yet another object is to provide an accurate and quick permanent record of assay results.

SUMMARY OF THE INVENTION

These and other objects are achieved by the present invention which is directed to an apparatus, kit and method for annotating information on an assay medium, such as an electrophoresis gel, thin-layer chromatography plate, and other chromatographies, X-ray film, densitometric scan, and the like, prior to recording the data on the assay medium by photography, photocopying, and other like means. In general, the apparatus includes means for retaining markers, the retaining means being adjacent an assay medium, and the markers operable to designate the lane of travel, location or other information about of a sample or separated components thereof, on the assay medium.

The apparatus is useful for indicating the lane of travel and position of a sample of a chemical, biological, agricultural material, and the like, or individual components thereof, separated on an assay medium, for example, by electrophoresis, thin layer chromatography, and other chromatographies, densitometric scan, and the like. The apparatus may also be used to indicate a notable area or section, or the position or location of one or more components on an assay medium, for example, in X-rays, charts, and the like. The assay medium with the location of a sample of components marked using the present apparatus may then be recorded by photography, videotaping, and the like, thus eliminating the arduous task of later marking individual photographs or other recordings of the medium.

In one embodiment, the apparatus is made of a planar base having first and second grooved tracks positioned perpendicular to each other in the planar base to define an assay medium receiving area thereinbetween, and at least two markers releasably attachable in the grooved track. The planar base may further include a third grooved track parallel the first track with the second track thereinbetween, or positioned perpendicular to the first track and parallel the second track, or a fourth track positioned perpendicular to the third track to define the assay medium thereinbetween.

The grooved tracks may be joined such that the track is continuous along two or more sides of the planar base, or may form discrete sections continuous along the entire or partial length of a side of the planar base. The markers may be inserted or slid into the grooved track and positioned along its length. The apparatus may further include one or more side rails having means for retaining a marker such as a grooved track or apertures, that may be placed adjacent to a side or on the surface of the planar base for use in designating information about the sample on the assay medium. In a preferred embodiment, a side rail includes means for inserting the rail into a grooved track in the planar base such that the rail can be positioned on the surface of the planar base as desired. The planar base may be made of any suitable material, for example an acrylic such as polymethacrylate.

In another embodiment, the apparatus is composed of two side rails positioned perpendicular to each other on a planar base to define an area for receiving an assay medium, i.e., assay medium receiving area, therein between, and at least two markers releasably attachable to the side rails. The apparatus may further include a third side rail that may be positioned on the planar base parallel to the first side rail with the second side rail thereinbetween, or positioned perpendicular to the first side rail and parallel to the second side rail. Preferably, the side rails are adjustable in relation to each other to vary the dimension of the assay medium receiving area to accommodate different sizes of assay media. The side rails may include means for attaching the rail to the planar base which preferably allows the location of the side rail on the base to be changed as desired, as for example, by a slidable connection between the side rail with a grooved track in the planar base.

The side rails include means for retaining the markers such as a grooved track, apertures, and the like. The markers positioned in or on the retaining means of the side rails operate to designate information about the sample in the assay medium, such as a sample lane or location of a sample or separated components thereof, to mark a particular area or element in the assay medium, or other like information. Preferably, the markers include a peg, and a side rail includes a grooved track continuous along part or all of its length such that the marker can be either inserted into or slid along the grooved track at any point along the length of the rail. In another embodiment, the side rail may have a plurality of discretely positioned apertures along part or all of its length into which the peg of the marker may be inserted.

The invention also includes an article of manufacture, or kit, comprising packaging material and the apparatus of the invention contained within the packaging material. The apparatus may be composed of a planar base with grooved tracks therein, and optionally a side rail; or two or more side rails for use in defining an assay medium receiving area on a surface of a planar base, and optionally a planar base; the apparatus further including at least two markers each having means for indicating location, identifying molecular weight, size, reactivity, and other the like information about the sample in the assay medium, and means for releasable attachment to the grooved tracks in the planar base, or to the side rails. Optionally, the kit may further include (a) instruction means comprising information relating to the use of the apparatus and other literature in the form of a label or tag attached to the packaging, or a printed package insert within the packaging; (b) means for recording the apparatus such as a camera; and/or (c) means for illuminating the apparatus such as a light source. In a preferred embodiment, the side rail has a grooved track continuous along at least part of its length into which the marker is placed by either sliding into the groove or inserting into the groove. In another embodiment, a side rail has a number of apertures positioned along at least part of its length, with the pegs of the markers insertable into the apertures.

A method of annotating a sample contained in an assay medium using the present apparatus, includes (a) providing a planar base with at least two perpendicularly arranged grooved tracks therein, which define an assay medium receiving area therebetween, and at least two markers; (b) inserting a marker into each of the grooved tracks; (c) placing the assay medium on the planar base within the assay medium receiving area; and (d) positioning the markers in the grooved tracks to denote information about a sample in the assay medium, and optionally, (e) providing a side rail with at least one marker, and placing the side rail adjacent to or on the surface of the planar base, and perpendicular to a grooved track to further define the assay medium receiving area, and then positioning the marker on the side rail to further denote information about the sample. Preferably the side rail includes means for releasably attaching the rail in one or more grooved tracks in the planar base, wherein step (e) further includes inserting the attachment means of the side rail into a grooved track in the planar base.

Another method according to the invention comprises (a) providing a planar base, at least two side rails, and at least two markers; (b) positioning the side rails on the planar base such that the side rails are aligned perpendicularly to each other to define an assay medium receiving area thereinbetween which has a surface area effective to receive the assay medium thereon; (c) attaching a marker to each of the side rails; (d) placing the assay medium containing the sample on the planar base within the assay medium receiving area; and (e) positioning the markers on the side rails to denote the location of or other information about the sample in the assay medium. Preferably the side rail includes means for releasably attaching the rail to a receiving means in the planar base, such as into one or more grooved tracks in the planar base, or apertures in the base, wherein the method further includes inserting the attachment means of the side rail into the receiving means in the planar base.

The apparatus and assay medium may then be photographed, videotaped, and the like, to produce a recording which shows the markers in the side rails adjacent the assay medium indicating the lane, location, and/or other information about a sample in the assay medium.

BRIEF DESCRIPTION OF THE DRAWINGS

Throughout the following views, reference numerals will be used in the drawings, and the same reference numerals will be used throughout the several views and in the description to indicate same or like parts of the invention.

DETAILED DESCRIPTION OF THE INVENTION

Figure 1:
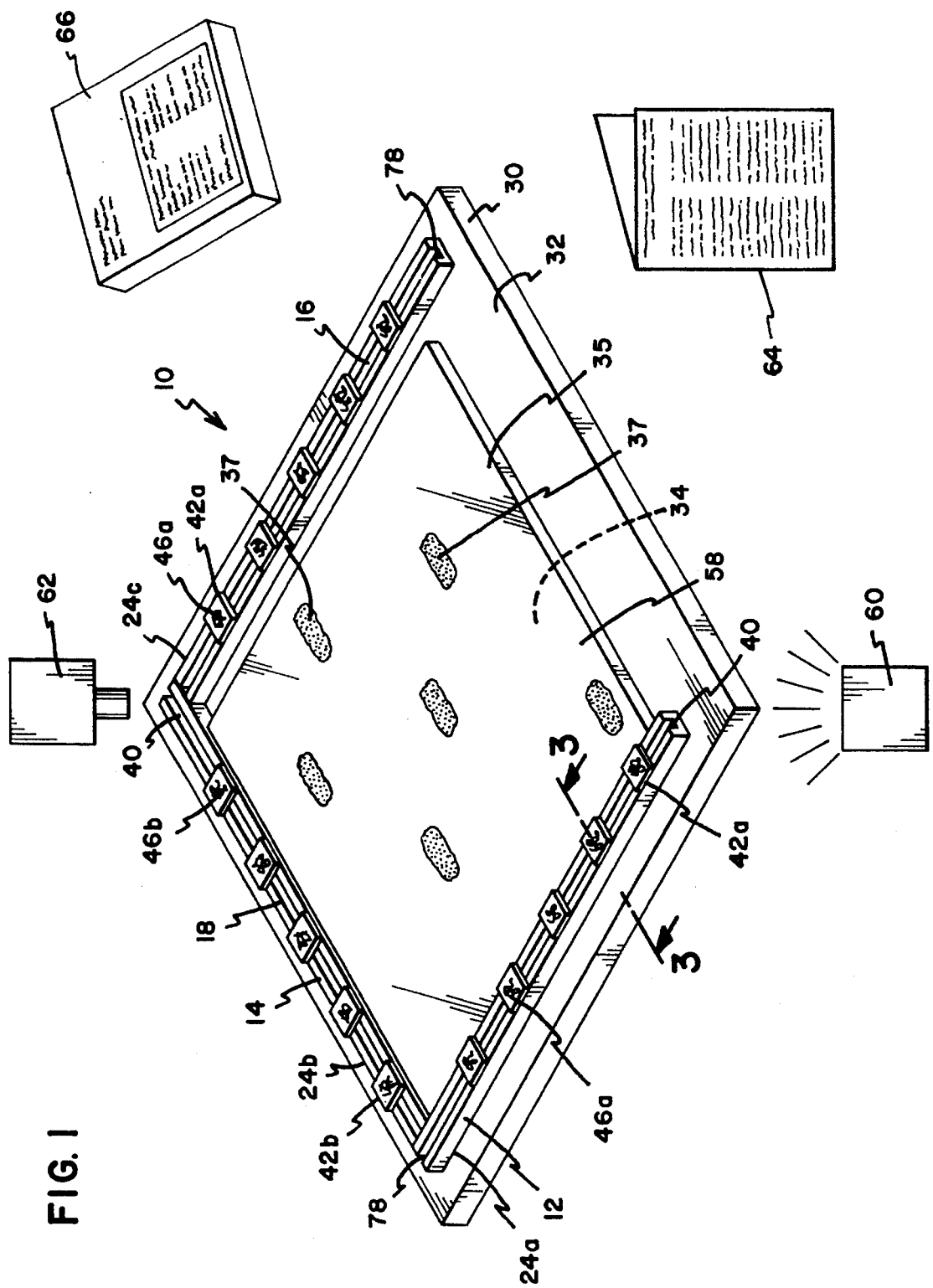
FIG. 1 is a perspective view of a first embodiment of an apparatus according to the invention showing side rails with grooved tracks positioned on a planar base adjacent an assay medium.

Referring now to FIG. 1, one embodiment of the apparatus for annotating an assay medium, designated generally as 10, is shown according to the present invention. It is understood, however, that a variety of shapes and sizes can be accommodated according to the invention.

The apparatus is useful for indicating the lane of travel and position of a sample or, as shown, the separated components of a sample, in the assay medium. The apparatus of the invention is useful for annotating assay media such as electrophoresis gels, chromatography papers and plates, gel matrices, densitometric scans, nitrocellulose blot papers and related materials used in blot assays, support membranes, X-ray films and plates, and the like, and related papers/ charts following separation by high or low pressure chromatography, prior to recording the results of the assay by photography, videotape, autoradiography, and the like.

Figure 2:
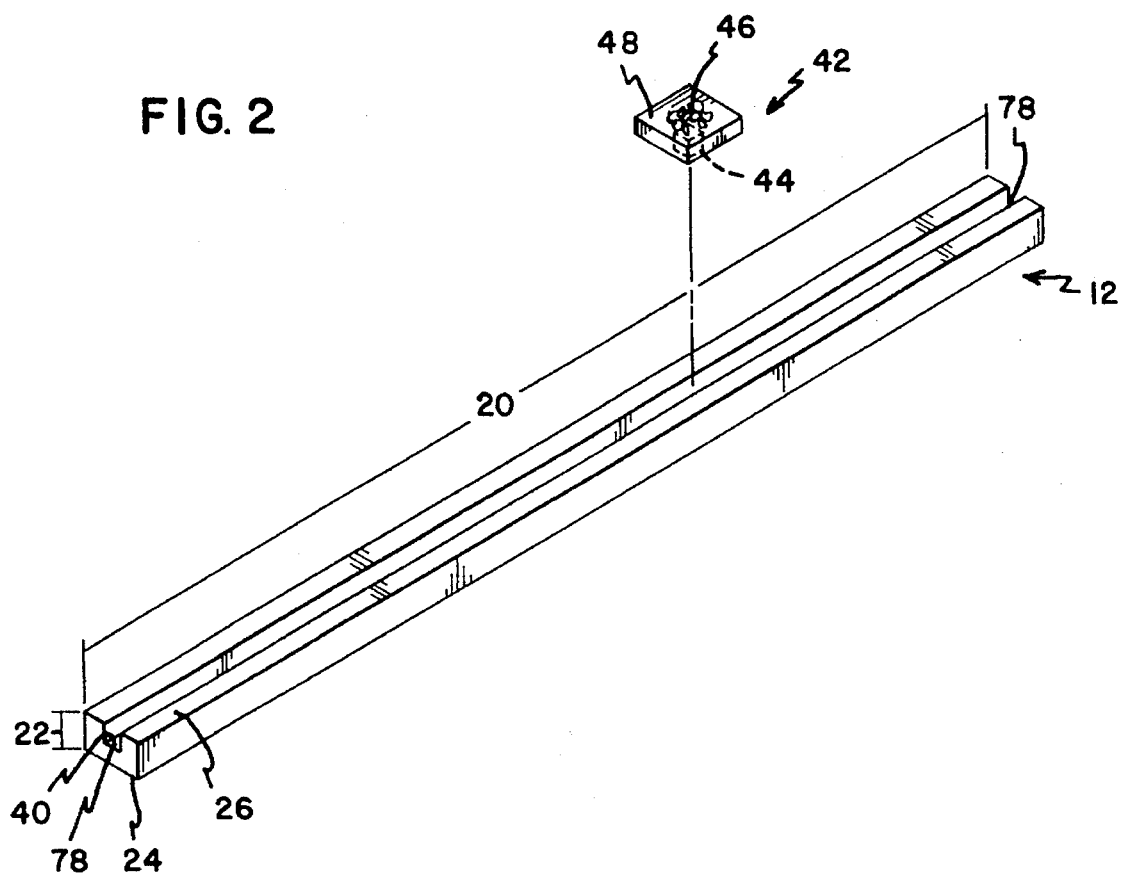
FIG. 2 is a perspective view of a side rail of the apparatus shown in FIG. 1.

Referring to FIG. 1, apparatus 10 is shown having three side rails, a first side rail 12, a second side rail 14, and a third side rail 16. A side rail according to the invention is illustrated in FIG. 2, and designated generally as 12. As shown, side rail 12 has a length 20, height 22, a first surface 24, and a second surface 26 having a grooved track 40 therein. In use, as shown in FIG. 1, the first surfaces 24a, 24b of side rails 12, 14, respectively, are placed in contact with surface 32 of a planar base 30, and the side rails 12, 14 positioned perpendicular to each other to define an assay medium receiving area 34 therebetween on which an assay medium 35 is placed. Optionally, as shown in FIG. 1, a third side rail 16 may be positioned on planar base 30, parallel first side rail 12 with second side rail 14 therebetween. The third side rail 16 may also be positioned perpendicular to first side rail 12 and parallel second side rail 14 (not shown). The apparatus may further include an optional fourth side rail (not shown) that may be positioned perpendicular the third side rail to further define the assay medium receiving area therebetween.

Figure 5:
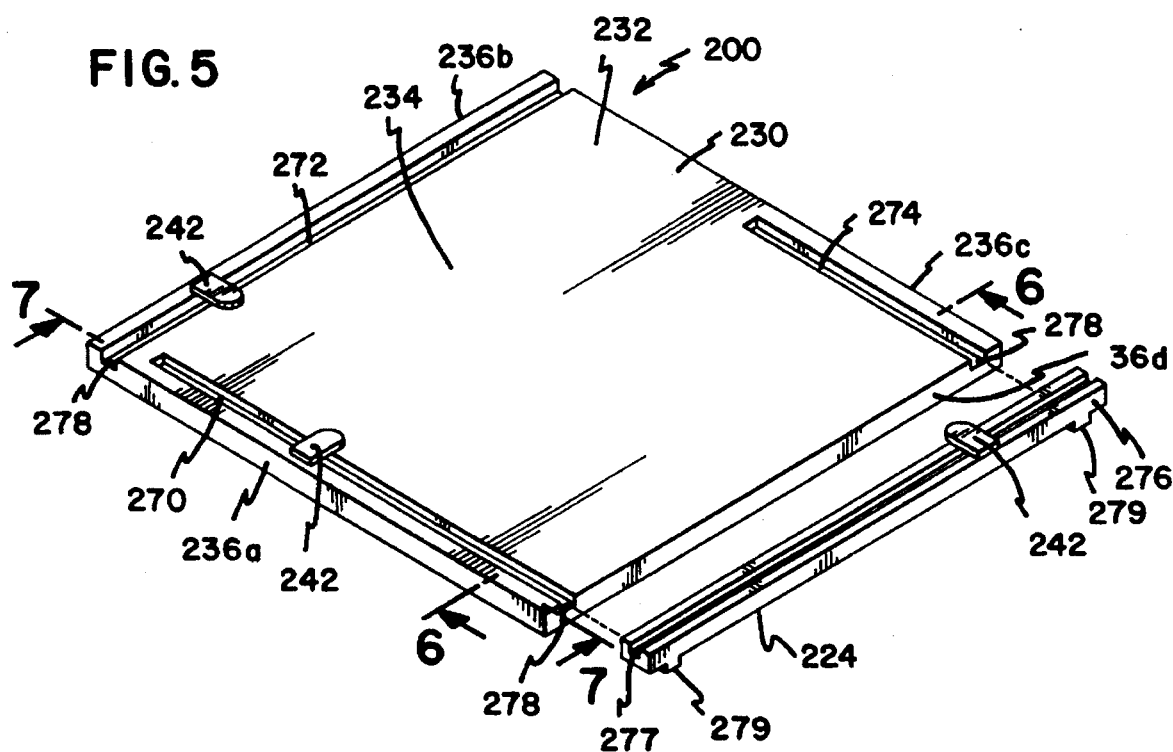
FIG. 5 is a perspective view of a third embodiment of an apparatus according to the invention showing grooved tracks in a planar base.

It is preferred that at least one side rail can be adjusted and repositioned in relation to another side rail on planar base 30 to define several sizes of an assay medium receiving area 34 on the surface 32 of planar base 30 and accommodate various sizes of assay media 35. In a preferred embodiment, a side rail includes means for releasably attaching the side rail to planar base 30 which would, in turn, include means for operably receiving the side rail attachment means. Such a connection may maintain the side rail in a substantially stationary location on the planar base, and also allow for repositioning the side rail on the planar base as desired. For example, as illustrated in FIG. 5, a side rail, shown as 276, may include an attaching means 279, shown as a U-shaped extension, affixed to first side 224 at one or both ends of side rail 276, and configured to be inserted or slid into one or both of grooved tracks 270 and 274 to position the side rail at a desired location on planar base 230. In another embodiment (not shown), a side rail may include attachment means in the form of one or more pegs for removable insertion into one or more apertures in the planar base. In yet another embodiment (not shown), a side rail and the planar base may include cooperative adhering means known and used in the art, such as cooperating Velcro™ strips.

The side rails may also include means for securing two rails together (not shown), such as a clasp, hinge, Velcro™, a male/female coupling attachment, holes drilled at intervals through the sides of one rail to accommodate a peg inserted therethrough into a hole in the end of a second rail, and other like connecting mechanisms. The dimensions of a side rail may be varied to accommodate assay media 35 of different lengths, widths and thicknesses. A side rail may be composed of an acrylic material such as polymethacrylate, wood, ceramic, glass, or a composite thereof, or other material that is chemically compatible, preferably inert, with the assay medium 35.

Figure 3:
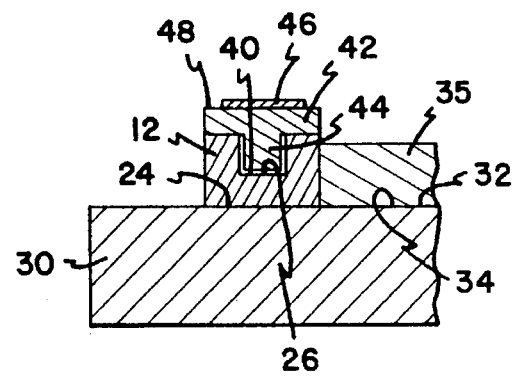
FIG. 3 is a cross-sectional view of a portion of the apparatus shown in FIG. 1, designated as 3—3, showing a pegged marker inserted into the grooved track of a side rail.

As shown in FIGS. 2 and 3, means for retaining a marker shown in the form of a grooved track 40 is located on the second surface 26 of the side rail, designated generally as 12. As shown, grooved track 40 is continuous along the length 20 of side rail 12 and configured to operably receive a plurality of pegged markers 42. In cross-section, grooved track 40 is shown in a U-shaped configuration. Pegged marker 42 is generally T-shaped in cross-section, and includes a peg 44 configured to be received within grooved track 40 for infinite adjustment in grooved track 40 for designation of lane, location, and other information about a sample 37 on the assay medium 35. Grooved track 40 and pegged markers 42 may be configured such that pegged markers 42 are slidable within grooved track 40, or such that pegged markers 42 are inserted into grooved track 40 and then withdrawn and reinserted to a different location as desired. Preferably, there is an opening 78 at one or both ends of the grooved track to facilitate sliding pegged marker 42 into the grooved track 40. The apparatus 10 may optionally include an end stop or other means that fits into opening 78 to retain pegged marker 42 in the grooved track 40 (not shown).

It is understood that grooved track 40 may be configured in any shape suitable to receive a pegged marker 42, for example, in a triangular shape to receive a similarly shaped peg 44, or with a groove to receive a peg 44 having a notch, and other like configurations (not shown). Pegged marker 42 may be formed of wood, plastic (i.e., plexiglass, polymethacrylate), ceramic, glass, metal and the like, with plastic or glass being preferred.

Pegged marker 42 includes means for indicating 46 for providing a letter, numeral, arrow, or other like indicia as desired. Indicating means 46 may be for example, a permanent or removable adhesive-backed indicia or label affixed to surface 48 of pegged marker 42, or an indicia molded, carved, imprinted and the like, into or onto surface 48. Indicating means 46 may be configured in any shape, may be colored, opaque, fluorescent, phosphorescent, and the like, and may be generally designed as desired. For example, indicating means 46 may be designed for use with a marker 42 for designating sample lanes along the width of the assay medium 35, with a marker 42 for designating molecular weights or other information about the relative position of a sample 37 and/or components thereof contained within the assay medium 35 along the length of the assay medium.

Figure 4:
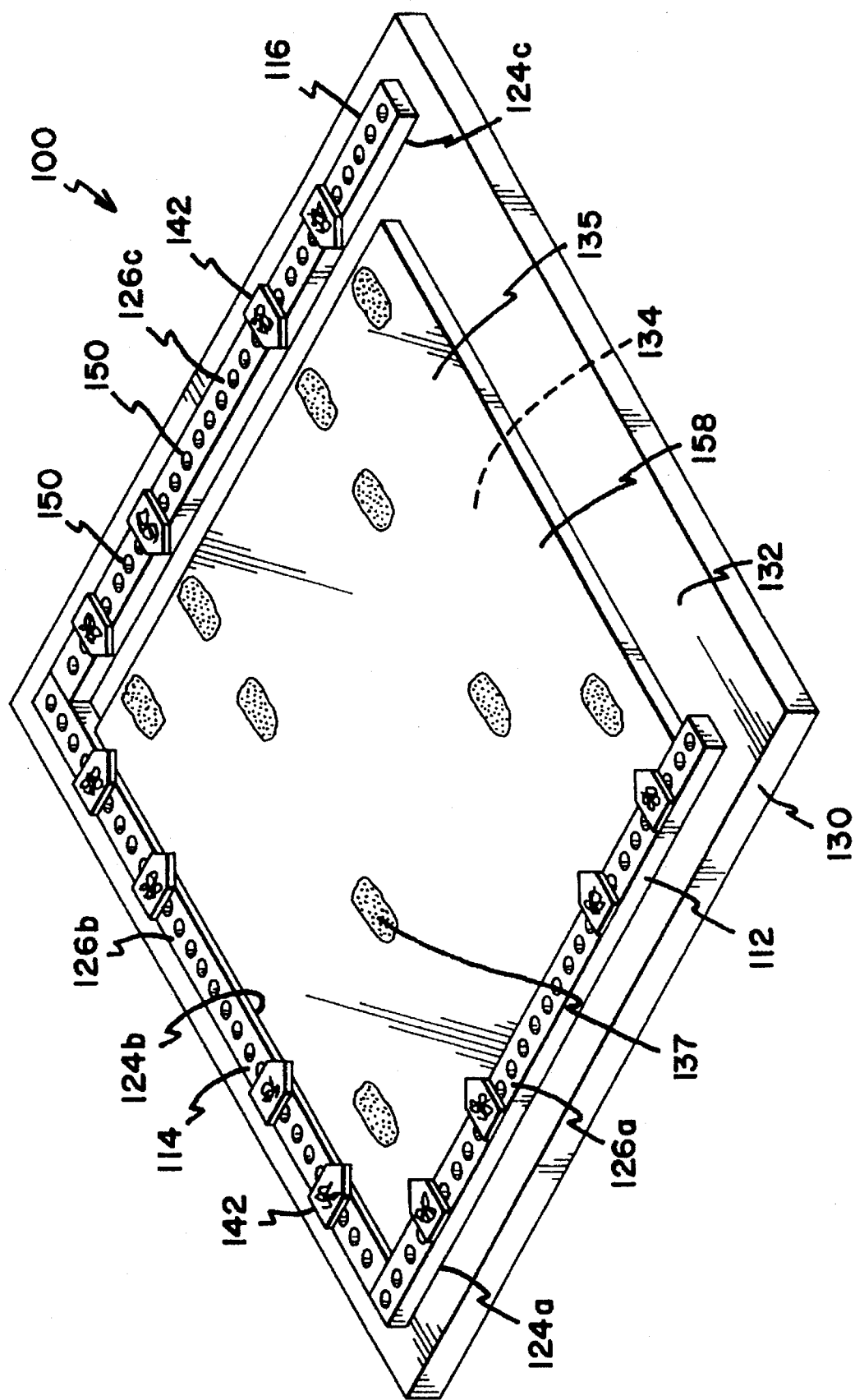
FIG. 4 is a perspective view of a second embodiment of an apparatus according to the invention, showing side rails with apertures positioned on a planar base adjacent an assay medium.

Alternative means for retaining a marker in a side rail is contemplated by the present invention. For example, as shown in FIG. 4, apparatus 100 with side rails 112, 114, 116, may include a plurality of discretely positioned apertures 150 on second surfaces 126a, 126b, 126c, respectively, continuous along all or part of the length of the side rail. A side rail may also contain apertures 150 in combination with a grooved track along a portion of its length, with pegs (not shown) of pegged markers 142 being configured to be inserted into the apertures 150 (not shown). In another embodiment (not shown), a marker may be constructed without a peg, but with means for releasably adhering to a flat or raised surface of a side rail. The marker may include a backing which will adhere to the surface of the side rail such as a releasable adhesive coating, a fabric such as vinyl or felt, metal, and the like. The marker and the side rail may have cooperative adhering means such as a velcro-type material, a metal and a magnetic material, and the like. The surface of the side rails for receiving a releasably adherent may be smooth or level, or include a grooved track or a raised portion continuous along the length of the rail, be inlaid or overlaid with a cooperative material, and the like. It is understood that a side rail may have a combination of retaining means for the markers. For example, part of the length may include a grooved track, and part include apertures or a smooth surface.

Figure 6:
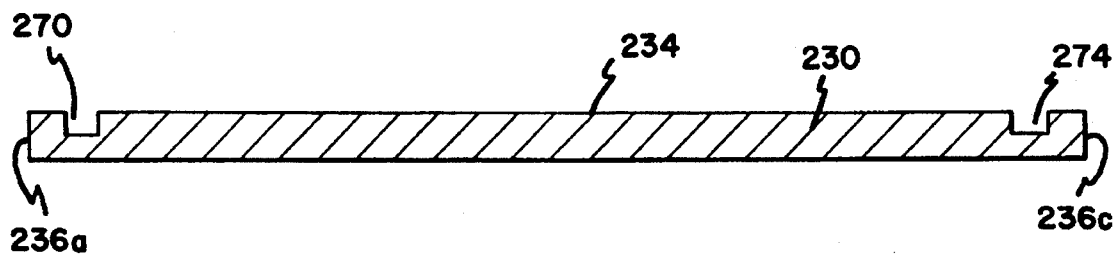
FIG. 6 is a cross-sectional view of the apparatus of FIG. 5, designated a 6—6.
Figure 7:
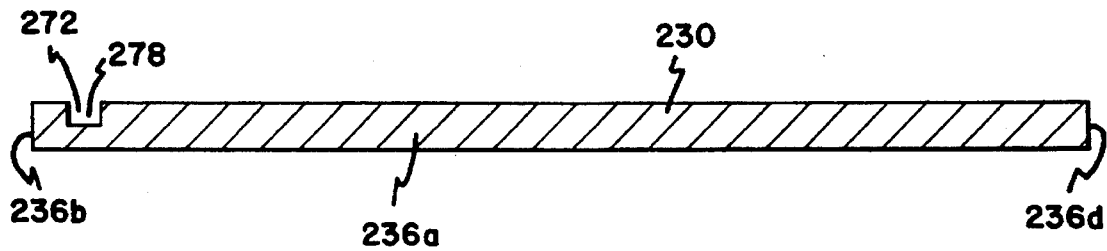
FIG. 7 is a cross-section view of the apparatus of FIG. 6, designated 7—7.

Another embodiment of the apparatus, designated generally as 200, is illustrated in FIG. 5. As shown, apparatus 200 has a planar base 230 with three grooved tracks, first grooved track 270, second grooved track 272, and an optional third grooved track 274. The grooved tracks 270, 272, 274 are positioned in the planar base 230 to define an assay medium receiving area 234 therebetween. The grooved track may be varied in length to be continuous along part or the entire length of a side 236 of the planar base 230. Preferably, there is an opening 278 at the end of the grooved track to facilitate sliding a marker 242 into the track. As shown in FIGS. 6 and 7, grooved tracks 270, 272, 274 of planar base 230 are U-shaped in cross-section, but may be of any shape to fit the configuration of the peg (not shown) of marker 242. Optionally, the apparatus 200 may include means for retaining a marker 242 in the grooved track (not shown), for example, an end stop that fits into opening 278. It is understood that an apparatus similar to 200 may be constructed with discretely positioned apertures in place of, or in combination with one or more grooved tracks in the planar base, with markers having pegs configured to be operably received in the apertures.

The apparatus 200 may further include one or more side rails, shown in FIG. 5 as 276 and having a grooved track 277 continuous along the entire length with at least one marker 242. The side rail 276 may be positioned along a side of planar base 230, shown, for example, as side 236. In a preferred embodiment, side rail 276 includes means 279 for attaching the side rail 276 to planar base 230. The attachment means 279 is affixed to first side 224 at one or both ends of the side rail 276, and is configured to be operably received within a grooved track for infinite adjustment on planar base 230 for defining variable sizes of an assay medium receiving area 234. As shown, attachment means 279 includes an extension at both ends of side rail 276, configured in a U-shape to be inserted or slid into grooved tracks 270, 274 on planar base 230.

The invention further provides an article of manufacture, i.e., a kit, for use in annotating samples in an assay medium according to the invention. The kit may include, contained within a packaging material, the apparatus 10 comprising first and second side rails 12, 14, which may be placed on the surface 32 of a planar base 30 to define an assay medium receiving area 34, and optionally a third side rail 16, and further a fourth side rail (not shown), each side rail having a grooved track 40; and two or more markers 42 which include indicating means 46 for designating information about the sample or its components in the assay medium 35 such as a sample lane, location, and the like. Optionally, the kit may further include (a) a planar base 30, preferably including means for operably and releasably receiving attachment means of a side rail to maintain the side rail in a substantially stationary position on the planar base during the annotating procedure; (b) instruction means 64 with information for assembling the side rails and markers on the planar base 30 in conjunction with an assay medium 35, for using the apparatus 10 for annotating the assay medium 35, for recording the assay medium 35 with apparatus 10, and other like literature; (c) a camera or other recording means 62; and/or (d) a light source 60 or other means for illuminating the apparatus 10. Element 66 is a not necessarily scale drawing of a package for holding an apparatus like that shown in the remainder of FIG. 1. Shown thereon is a label with printed instructions which can be used as an alternative to sheet instructions 64.

Another kit according to the invention, may be composed of apparatus 150 with side rails 112, 114, and optionally side rail 116 or a fourth side rail, each having apertures for receiving markers 142 therein. It is understood that a kit may contain a combination of side rails having a combination of marker retaining means such as a grooved track and/or apertures and/or adhering means along its length, with corresponding markers to cooperate with the marker retaining means of a side rail. Yet another kit according to the invention includes apparatus 200 made of a planar base 230 having grooved tracks 270, 272 therein, and optionally, grooved track 274, a fourth grooved track (not shown), and/or one or more side rails each with a marker 242, the side rail having retaining means for the marker, and, preferably, means for inserting the side rail in one or more grooved tracks in planar base 230.

An example of the apparatus of the invention in use is illustrated in FIG. 1. As shown, first surfaces 24a, 24b, 24c of side rails 12, 14, 16, respectively, of apparatus 10 are positioned on surface 32 of planar base 30 with at least a portion of planar base 30 framed by the side rails 12, 14, 16 to define an assay medium receiving area 34 therebetween. Planar base 30 is preferably transparent to visible and/or ultraviolet light. Planar base 30 may be constructed out of a transparent acrylic, preferably polymethacrylate, glass, or other like material chemically compatible with the assay medium, with polymethacrylate being preferred. Planar base 30 may also be a nontransparent material such as wood, which would require side and/or top lighting for illuminating the apparatus and assay medium. Planar base 30 may be constructed with an associated light source used for viewing stained gels, autoradiograms, microtiter plates, slides, overhead transparencies, and the like, such as a transilluminator, portable light table or other like device are commercially available, for example, from Research Products International Corp., Mt. Prospect, Ill. Preferably, side or top lighting is used with an assay medium comprising nitrocellulose or other non-transparent material, with the assay material resting on planar base 30.

As shown, side rails 12, 16 are positioned on planar base 30, parallel to one another, with side rail 14 perpendicularly positioned therebetween. Side rails 12, 14, 16, in combination on planar base 30, define a frame 18 and an assay medium receiving area 34 therebetween. Side rails 12, 14, 16, may be dimensioned according to the length, width, and/or thickness of the assay medium. In a preferred embodiment, at least one of side rails 12, 14, 16 can be moved relative to each other on planar base 30. By moving one side rail, for example third side rail 16, the size of the assay medium receiving area 34 may be adjusted to accommodate different sizes of assay media 35. While in a preferred embodiment three side rails 12, 14, 16 are used, generally only two side rails, 12 and 14, are necessary to the operation of the present invention. Third side rail 16 may also be positioned perpendicular to first side rail 12 and parallel to second side rail 14. A fourth side rail (not shown) may also be positioned perpendicular to third side rail 16 on a planar base 30, to further define the assay medium receiving area 34 therein between.

Preferably, one or more side rails include means for releasably attaching the side rail to planar base 30 which, in turn, includes means for operably and releasably receiving the attachment means 279 of the side rail. For example, a side rail, such as 276 in FIG. 5, shown as having attachment means 279 in the form of an extension at both ends of side rail 276, may be inserted or slid into grooved tracks 270 and 274 and positioned on surface 232 of planar base 230 to define an assay medium receiving area 234 as desired. In another example (not shown), side rails 12, 14 may include discretely spaced pegs affixed to first surfaces 24a, 24b, respectively, which may be removably inserted into discretely spaced apertures in planar base 30, with side rail 16 being slidable on surface 32 of planar base 30 to define various sizes of an assay medium receiving area 34.

The assay medium 35 containing a sample or separated components thereof, shown generally as 37, is placed on planar base 30 within assay medium receiving area 34, bounded by side rails 12, 14, and optionally a side rail 16, and further a fourth side rail as desired. The side rails may be adjusted on the planar base 30 so that the rails are positioned in close proximity to or in contact with the assay medium 35.

As shown in FIG. 1, one or more pegged markers 42b with indicating means 46b are placed in grooved track 40 of second side rail 14 to designate and correspond with, for example, the individual lane of travel of each sample in an electrophoresis gel or chromatography assay medium, the row or column of a sample in a dot blot assay medium, a peak of a sample in a gas chromatography sheet, to define a scale, and/or identify the location of standards such as molecular weights standards, environmental standards, and the like. The pegged markers 42b with indicating means 46b are adjusted along second side rail 14 such that one pegged marker 42b designates a single lane, column, row, peak and the like, of a sample 37 in the assay medium 35. One or more pegged markers 42a with indicating means 46a are positioned in grooved track 40 of first side rail 12, and/or optional third side rail 16, to designate the relative locations, molecular weights or other information about the samples 37 or separated components thereof in the assay medium 35, such that each marker 42a designates a single component of sample 37, or multiple, overlapping or intersecting samples.

To record an assay medium in conjunction with the apparatus, a recording device such as a camera, videocamera, photocopier, and the like, shown generally as 62 in FIG. 1, may be used. Autoradiographic techniques may be used with markers 42 that are active on X-ray film. Preferably, means for illuminating the apparatus, shown in FIG. 1 as light source 60, is positioned in relation to planar base 30 (i.e. beneath, as shown, and/or above or to the side (not shown)) to transmit an amount of light effective to illuminate the apparatus 10 and the assay medium 35 on the assay media receiving area 34. For example, after staining, a polyacrylamide electrophoresis gel remains translucent while the, sample components, such as proteins, carbohydrates, lipids, nucleic acids, and the like, as separated bands on the medium will bind the dye and be rendered opaque. Samples transferred to nitrocellulose paper which are hybridized to a radiolabel or antibodies and/or autoradiographed, are preferably illuminated with a side and/or top light, and will appear as darkened bands on an opaque background. Illuminating means 60 illuminates the apparatus and assay medium receiving area 34 and enhances visualization of the sample 37 in the assay medium 35 when viewing and recording the assay medium. To avoid blurring between the images of the sample in the assay medium and the indicia on the pegged markers when recording the apparatus and assay medium, the exposed surface 58 of the assay medium 35 should be within the planar focus of the indicating means of the pegged marker.

Advantageously with the present apparatus, sections of the assay medium may be cut apart and separated, an undesirable section may be optionally eliminated, and then the sections rearranged as desired in relation to each other on the planar base in the assay medium receiving area. The appropriate marker may then be placed in a side rail or grooved track, and matched with its corresponding sample lane, or other section of the assay medium, and the assay medium recorded.

EXAMPLE

An apparatus for annotating an electrophoresis gel was constructed out of a sheet of plexiglass, 5.25×4.5×0.2 inches (133×114×6 mm) (w×l×d) as a planar base with 0.15-inch (4 mm) square grooved tracks located on three sides. The grooved tracks were each cut into the plexiglass as illustrated in FIG. 5, except that the tracks extended along the entire width/length of the base, and intersected each other.

Pegged markers, 7×20×3 mm (w×l×d) with an attached 4mm square peg were constructed out of clear polycarbonate. Rub-on numbers were affixed to the surface of the markers to indicate (i) the sample lane, and (ii) the position of the molecular weight standard in the electrophoresis gel. The pegged markers easily slid in the grooved track, and could be aligned with a sample lane, or a molecular weight marker that migrated in a standard polyacrylamide gel electrophoresis (PAGE), a sodium dodecyl sulfate polyacrylamide gel electrophoresis (SDS-PAGE), or an agarose electrophoresis gel.

A 10% SDS-PAGE gel was prepared according to a standard protocol. High molecular weight markers (Sigma) were applied to the gel and electrophoresed. The gel was stained with 0.25% Coomassie Brilliant Blue, and destained in 50% methanol, 10% acetic acid. Following destaining, the gels were placed in a 10% glycerol, 7% acetic acid solution to allow the gel to swell.

The gel was placed on the plexiglass base, framed by the three grooved tracks. The pegged markers were slid into the grooved track and aligned with the sample lane (as in grooved track 272 shown in FIG. 5), and the corresponding molecular weight marker in the gel (as in grooved tracks 270, 274 shown in FIG. 5). The gel and apparatus were illuminated with a light source placed underneath the plexiglass base, and photographed with a 35 mm camera positioned overhead the plexiglass base and assay medium.

The invention has been described with reference to various specific and preferred embodiments and techniques. However, it should be understood that many variations and modifications may be made while remaining within the spirit and scope of the invention.

What is claimed:

1. An apparatus for annotating an assay medium containing a sample located thereon, the apparatus comprising:
   (a) a planar base having a surface with first and second grooved tracks therein, each track having a length, depth and width; the grooved tracks aligned perpendicular to each other in the planar base to define an assay medium receiving area therebetween; and
   (c) at least two markers, a first marker being releasably attached in the first grooved track, and a second marker being releasably attached in the second grooved track; the markers being positionable along the grooved tracks and including indicating means to designate information about the sample or separated components thereof in an assay medium placed on the assay medium receiving area.

2. The apparatus according to claim 1, further comprising a side rail having a length, and first and second surfaces, and means for operably and releasably retaining a marker in said second surface of the side rail; the side rail being positioned on the surface of or adjacent to the planar base to operably receive the marker in said marker retaining means to designate information about the sample in the assay medium; the side rail being aligned perpendicular to the first or second grooved track to further define the assay medium receiving area.

3. The apparatus according to claim 2, wherein the side rail further includes means for attaching the side rail to the planar base, said attachment means being affixed to the first surface of the side rail; said attachment means being releasably attached in the first or second grooved track in the planar base, and positionable on the surface of the planar base along the grooved track to further define the assay medium receiving area.

4. The apparatus according to claim 3, wherein the side rail is slidable within the first or second grooved track.

5. The apparatus according to claim 3, wherein the planar base further includes a third grooved track therein being aligned perpendicular to the first or second grooved track to further define the assay medium receiving area, wherein the attachment means of the side rail is releasably attached in the third grooved track.

6. The apparatus according to claim 2, wherein the marker retaining means of the side rail is a grooved track being continuous along at least part of the length of the side rail, or a plurality of discretely positioned apertures along at least a part of the length of the side rail, or a combination thereof.

7. The apparatus according to claim 1, further comprising a plurality of markers being releasably attached in the grooved tracks in the planar base, and positionable along said grooved tracks to designate information about two or more samples or separated components thereof in the assay medium.

8. The apparatus according to claim 1, wherein the markers comprise a peg, and the grooved tracks of the planar base are configured to operably and releasably receive the peg of the marker.

9. The apparatus according to claim 8, wherein the markers are slidable within at least one of the grooved tracks.

10. The apparatus according to claim 1, wherein the planar base is transparent to visible or ultraviolet light.

11. The apparatus according to claim 1, in combination with an assay medium positioned on the surface of the planar base within the assay medium receiving area.

12. The apparatus according to claim 1, further comprising means for illuminating the apparatus, being positioned Above, under or to a side of the planar base.

13. The apparatus according to claim 1, further comprising means for recording the apparatus, being positioned above, under or to a side of the planar base.

14. The apparatus according to claim 13, wherein said means for recording is a camera, videotape, autoradiographic means, digital scanning, or photocopying device.

15. An article of manufacture for use in annotating an assay medium containing a sample thereon, comprising, in combination, packaging material and an apparatus according to claim 1 contained within said packaging material.

16. The article according to claim 15, further comprising instruction means which indicate how to assemble, use, or record the apparatus, or a combination thereof.

17. The article according to claim 16 wherein the instruction means is a label or tag attached to the packaging.

18. The article according to claim 16, wherein the instruction means is a printed package insert.

19. The article according to claim 15, further comprising means for recording, means for illuminating, or a combination thereof.

20. A method of annotating an assay medium containing a sample thereon, the sample having a location in the assay medium, the method comprising:
   (a) providing a planar base having first and second grooved tracks therein, and at least two markers; the grooved tracks each having a length, depth, and width, the grooved tracks aligned perpendicular to each other in the planar base to define an assay medium receiving area therebetween; the assay medium receiving area having a surface area effective for receiving the assay medium thereon;
   (b) attaching a first marker to the first grooved track, and a second marker to the second grooved track; the markers being releasably attached to the grooved tracks;
   (c) placing the assay medium containing the sample on the planar base within the assay medium receiving area; and
   (d) positioning the first marker in the first grooved track and the second marker in the second grooved track to denote information about the sample in the assay medium.

21. The method according to claim 20 wherein the sample comprises a plurality of separate components in the assay medium; and the apparatus comprises a plurality of first markers in the first grooved track and a plurality of second markers in the second grooved track; the method further comprising adjusting the markers along the lengths of the grooved tracks to designate information about the components of the sample in the assay medium.

22. The method according to claim 21, further comprising step (e) recording the markers and the sample in the assay medium.

23. The method according to claim 22, wherein the markers and the sample in the assay medium are recorded by photographing, videotaping, autoradiographic technique, digital scanning, or photocopying.

24. The method according to claim 22, further comprising illuminating the assay medium prior to and during the recording.

25. The method according to claim 20, further comprising:
   (e) positioning a side rail on the surface of or adjacent to the planar base, wherein the side rail is aligned perpendicular to the first or second grooved track to further define the assay medium receiving area; the side rail having a first and second surface, a length, and means for operably and releasably receiving a marker on said second surface of the side rail; the second surface of the side rail being positioned for operably receiving a marker in said marker receiving means;

(f) attaching a marker to said receiving means and positioning the marker on the side rail to designate information about the sample in the assay medium.

26. The method according to claim 25, wherein the side rail further includes means for releasably attaching the side rail to the planar base, said attachment means affixed to the first surface of the side rail; and step (e) further comprises inserting said attachment means into the first or second grooved track in the planar base, and positioning the side rail on the surface of the planar base along the grooved track to further define the assay medium receiving area.

27. The method according to claim 26, wherein the planar base further includes a third grooved track aligned perpendicular to the first or second grooved track; and the side rail includes attachment means operable for further inserting the side rail in the third grooved track; and step (e) further comprises attaching said attachment means in the third grooved track.

* * * * *